(12) United States Patent
Poezevera

(10) Patent No.: US 7,400,921 B2
(45) Date of Patent: Jul. 15, 2008

(54) DETECTION, ANALYSIS AND TREATMENT OF VENTRICULAR PAUSES IN AN ACTIVE IMPLANTABLE MEDICAL DEVICE FOR THE TREATMENT OF HEARTBEAT RATE DISORDERS

(75) Inventor: Yann Poezevera, Courcouronne (FR)

(73) Assignee: ELA Medical S.A.S., Montrouge (FR)

( * ) Notice: Subject to any disclaimer, the term of this patent is extended or adjusted under 35 U.S.C. 154(b) by 460 days.

(21) Appl. No.: 10/236,080

(22) Filed: Sep. 4, 2002

(65) Prior Publication Data
US 2003/0060852 A1 Mar. 27, 2003

(30) Foreign Application Priority Data
Sep. 4, 2001 (FR) ................... 01 11396

(51) Int. Cl.
*A61N 1/362* (2006.01)
(52) U.S. Cl. .......................... 607/9; 600/509
(58) Field of Classification Search .......... 607/4, 607/9, 16; 600/508–510, 515, 519, 71
See application file for complete search history.

(56) References Cited

U.S. PATENT DOCUMENTS

| 5,261,401 A | 11/1993 | Baker et al. |
| 5,306,293 A | 4/1994 | Zacouto |
| 7,039,461 B1 * | 5/2006 | Lovett .................. 607/14 |

FOREIGN PATENT DOCUMENTS
EP  0 472 411 A1  2/1992

* cited by examiner

*Primary Examiner*—Carl H. Layno
*Assistant Examiner*—Brian T Gedeon
(74) *Attorney, Agent, or Firm*—Orrick Herrington & Sutcliffe, LLP

(57) ABSTRACT

An active implantable medical device for the treatment of heartbeat rate disorders including the detection, analysis and treatment of ventricular pauses. The device includes circuits for delivering ventricular stimulation, circuits for detecting a normal spontaneous ventricular cardiac activity; a circuit for controlling ventricular stimulation that is suitable to control the application of a stimulation in the absence of normal spontaneous ventricular activity; and the continuous recording of the current cardiac information, such as detected cardiac activity and/or of parameters representative of those events. It also includes an algorithm for the controlled inhibition of the ventricular stimulation such that ventricular pauses of a duration greater than a predetermined value (X) are detected, wherein the predetermined value evolves over time in a progressive manner, and the ventricular pauses occur during the periods of controlled inhibition of the ventricular stimulation. The last recorded current cardiac events and/or event markers preceding a detection of the ventricular pause are preserved. Also, stimulation at a physiological back-up frequency is provided in the event of a detected ventricular pause.

10 Claims, 2 Drawing Sheets

DETECTION, ANALYSIS AND TREATMENT OF VENTRICULAR PAUSES IN AN ACTIVE IMPLANTABLE MEDICAL DEVICE FOR THE TREATMENT OF HEARTBEAT RATE DISORDERS

FIELD OF THE INVENTION

The present invention relates to "active implantable medical devices" as such devices are defined by the Jun. 20, 1990 directive 90/385/CEE of the Council of the European Communities. It relates more particularly to pacemaker, defibrillator and/or cardiovertor devices that are in particular equipped with that is known as "Holter" memory functions that allow a continuous monitoring of the of heartbeat rate parameters, as well perhaps as the memorizing of marker codes corresponding to those events (such as stimulation, detection in or out of a refractory period, sensor, etc.), known as event markers, to evaluate the stability of the heartbeat rate for diagnostic and/or therapeutic purposes.

BACKGROUND OF THE INVENTION

Certain patients present in a paroxystic manner symptoms of a bradycardia condition, such as unexplained syncopes, but without a presenting bradycardia condition that can be observed and documented by a conventional temporary external recording of the Holter type.

To make it possible for a practitioner to pose a diagnosis and to decide whether a pacemaker implant is an appropriate therapy, it has been proposed to implant a device with purely diagnostic objectives, making it possible to record information of the heartbeat rate in order to confirm whether various symptoms observed in the patient have a "rhythmic cause," that is, a heartbeat rhythm (or lack of rhythm) that leads to the observed symptoms that is detected and to be treated. One such device is the Reveal® Insertable Loop Recorder, available from Medtronic, Inc. However this device does not comprise any means for providing cardiac stimulation and is designed not to have an endocardial probe so as to simplify its implantation. Therefore, this device does not offer any help in the event of an occurrence of a severe bradycardia whose consequence can be extremely noxious for patients having a risk of ventricular arrhythmia.

It would be certainly possible to implant in the patient, on a purely prophylactic basis, a complete pacemaker equipped with suitable Holter memory functions. Such an apparatus, initially, could then be used only for its Holter capabilities, in order to record information on the heartbeat rate at the time the symptoms are evoked by the patient, in order to confirm or not whether the symptoms have a rhythmic cause. But to be able to record the spontaneous cardiac activity of the patient, it is of course necessary to inhibit the cardiac stimulation function of the pacemaker device. In this example, it is not convenient to activate the stimulation means, because the indication for a therapeutic stimulation by the apparatus has not yet been demonstrated; however, according to the patient, the presence of a pacemaker and the acceptance of a surgical operation for its implantation make intolerable the persistence of symptoms that are sometimes severe, and whose consequences can be extremely serious. It would be thus essential in this example to envisage providing a back-up ventricular stimulation.

However, a traditional pacemaker would not be adapted to this situation. Indeed, the base stimulation frequency cannot be programmed with a sufficiently low value to let the spontaneous ventricular rhythm be expressed at the time of a bradycardia. And, even if the pacemaker could have a rather low base frequency value, that value would be fixed and arbitrary, and could thus appear insufficient or unsuited for the patient. It is indeed not possible to define a priori the ventricular back-up stimulation frequency, which must be sufficiently low so as not to disturb the recording of the spontaneous cardiac activity, and sufficiently high not to let too severe a bradycardia be expressed.

The compromise sought is thus impossible to find in a general manner, because the threshold of the severity of a bradycardia giving rise to symptoms is specific to each patient.

OBJECT AND SUMMARY OF THE INVENTION

It is, therefore, an object of the present invention to overcome the above-mentioned disadvantages, by proposing a device that is able to search for ventricular pauses in a progressive and adaptive manner, in order to approach more closely the symptomatic threshold that is specific to the patient at the moment considered, while ensuring delivery of a back-up stimulation pulse as the recording is being carried out.

One aspect of the present invention is directed toward a modification of an implant of the type including: means for delivering a ventricular stimulation pulse as deemed appropriate; means for detecting a spontaneous ventricular cardiac activity; means for controlling the ventricular stimulation pulse delivery means, suitable to control the application of a given stimulation pulse or pulses in the absence of detected spontaneous ventricular cardiac activity; and means for continuously recording current cardiac information, such as detected cardiac activity or of parameters that are representative of thase that activity (i.e., event markers), or both.

According to the present invention, the device also includes: means for providing a controlled inhibition of the ventricular stimulation means; means for detecting one or more ventricular pauses of a duration greater than a predetermined value, the aforementioned predetermined value being one that is evolving over time in a progressive manner, the aforementioned ventricular pauses occurring during periods of controlled inhibition of the ventricular stimulation means; and means for safeguarding (i.e., preserving in memory) the last current cardiac events and/or event markers recorded for an interval preceding the detected ventricular pause.

In a preferred embodiment, the implant device is of the double-chamber pacemaker type, which makes it possible to better determine the heartbeat rate disorder that causes the bradycardia. Indeed, the presence of an endocardial probe in the atrium and the sensing of the cardiac potential in the atrium makes it possible to refine the origin of any bradycardia by distinguishing, for example, a sino-atrial block from a block at the level of the bundle of His or from a branch block. For this purpose, the device also preferably includes means for detecting an atrial cardiac activity and means for discriminating the origin of the bradycardia causing the heartbeat disorder rate.

According to various subsidiary and advantageous characteristics of alternate embodiments, a device in accordance with the present invention also may include one or more of the following:

means for controlling the stimulation means to operate at a physiological back-up stimulation frequency in the event of a detected ventricular pause;

means for gradually reducing said predetermined value by successive steps after a detected ventricular pause, said reduction being operated repeatedly until a programmed minimum threshold is reached, and being in particular operated only after the preliminary detection of a normal spontaneous ventricular cardiac activity;

means for permanently deactivating, after safeguarding the last current cardiac events and/or event markers recorded prior to the detected ventricular pause, said controlled inhibition means of the ventricular stimulation means, the permanent deactivation being in particular used only until the aforementioned programmed threshold was reached and after the preliminary detection of a normal spontaneous ventricular cardiac activity.

DETAILED DESCRIPTION OF THE INVENTION

The present invention can be advantageously implemented in an existing implant such as pacemaker, defibrillator and/or cardiovertor that is a microprocessor controlled device operating under the control of software, the particular functions of the invention being implemented by a suitable programming of the software.

Figure 2:
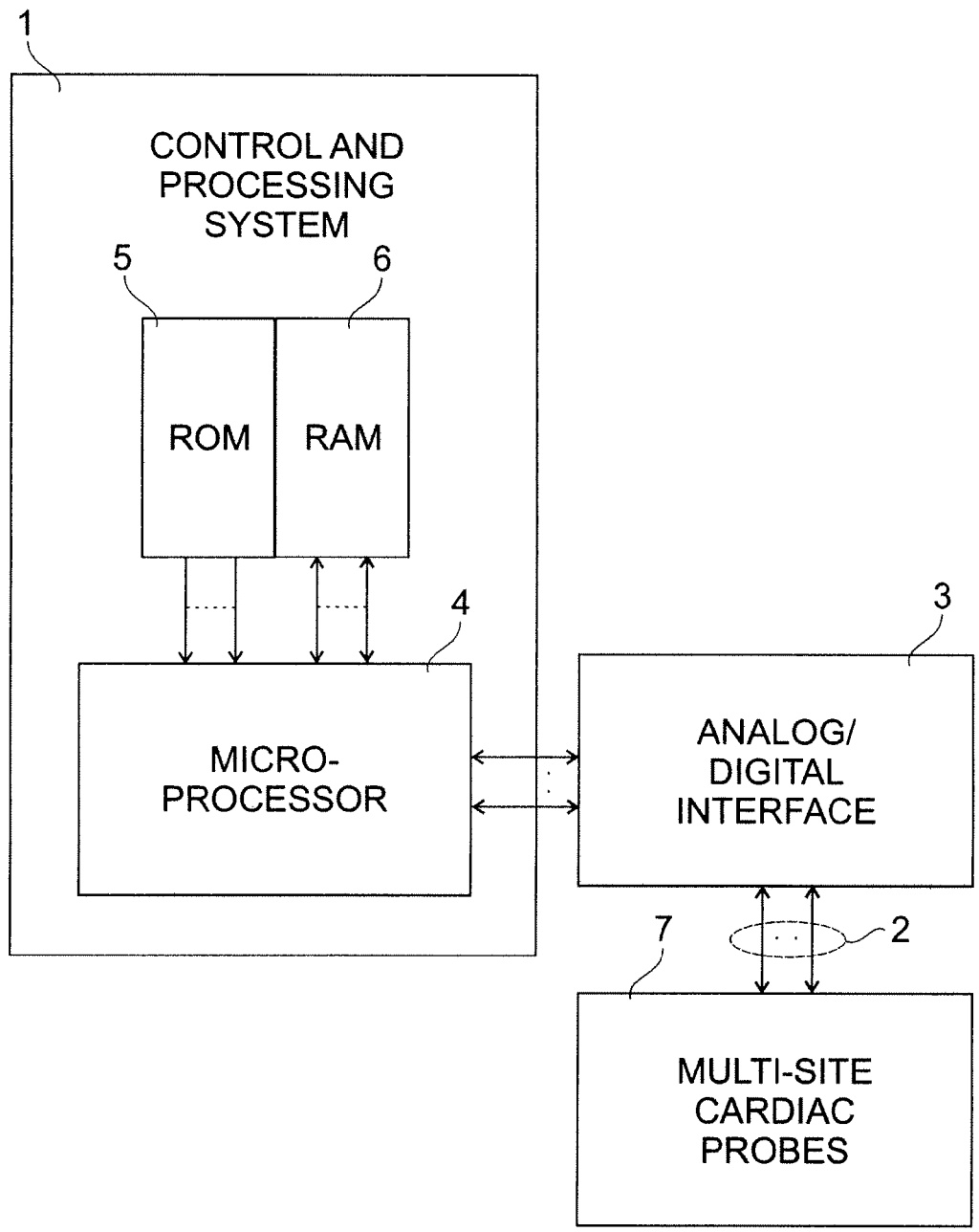
FIG. 2 illustrates schematically the general use of a typical pacemaker of multi-site type.

FIG. 2 illustrates in block form the typical structure of a pacemaker of this type, including a control and processing system 1, multiple leads 2 connected to probes at cardiac sites, an analog/digital interface for transferring the analog signals from the leads 2 to the micro-processor 4 and vice versa, a micro-processor 4 for the processing of instructions necessary in implementing the algorithm of the present invention, ROM 5 and RAM 6 for storing the software instructions and data for implementing the algorithm of the present invention, and cardiac probes 7 placed at multiple cardiac sites as is typical of known multi-site pacemakers.

These devices, in a known manner, are equipped with ventricular stimulation means, i.e., circuits for delivering one or more stimulation pulses to the ventricle, as well as with means making it possible to detect the presence or absence of spontaneous ventricular cardiac activity (i.e., circuits for sensing cardiac activity relative to a threshold) and, in the affirmative, to analyze the character of the detected spontaneous activity (i.e., as normal or abnormal, regular and coherent cycles, frequency in conformity with the activity of the patient, etc.). If the detected spontaneous activity is absent or abnormal, the ventricular stimulation means is then controlled in a suitable manner so as to apply to the myocardium a pulse having an energy that is able to cause the depolarization of the myocardium at a time that is determined by the software controlling the pacemaker (or other implant). The creation of suitable software instructions for controlling an implant to perform the aforementioned functions of the present invention are within the abilities of a person of ordinary skill in the art.

The implant device of the present invention is also equipped with Holter functions, allowing a continuous monitoring of the heartbeat rate parameters, as well as the so-called event markers, recording such data in RAM 6. Generally, being an implanted device, the recording storage capacity is limited, and therefore one provides to operate the recording in a loop. In other words, as long as the recording of current data continues, the most recent data acquired replaces the oldest data previously recorded (once the designated Holter memory capacity is full).

Primarily, the present invention concerns modifying the known devices to inhibit the delivery of any stimulation pulse so as to let the spontaneous cardiac rhythm be expressed and thus allow the occurrence of ventricular pauses. As soon as a ventricular pause is detected, the last several minutes of the heartbeat rate information recorded in the memory of implant are preserved for the purpose of later analysis so that the practitioner can determine the cause of the ventricular pause, e.g., whether of cardiac origin or not, and decide whether it is convenient or appropriate to activate in a permanent manner the stimulation functions of the device.

More preferably, a control algorithm is provided, as will be described, for use in the device that makes it possible to search for ventricular pauses in a progressive manner, in order to approach more closely the symptomatic threshold, while being certain to be able to apply to the patient a back-up stimulation pulse each time that a ventricular pause is detected. With this intention, according to the invention, the device is equipped with a variable base stimulation frequency that is slowly decreased progressively at each detected ventricular pause.

Figure 1:
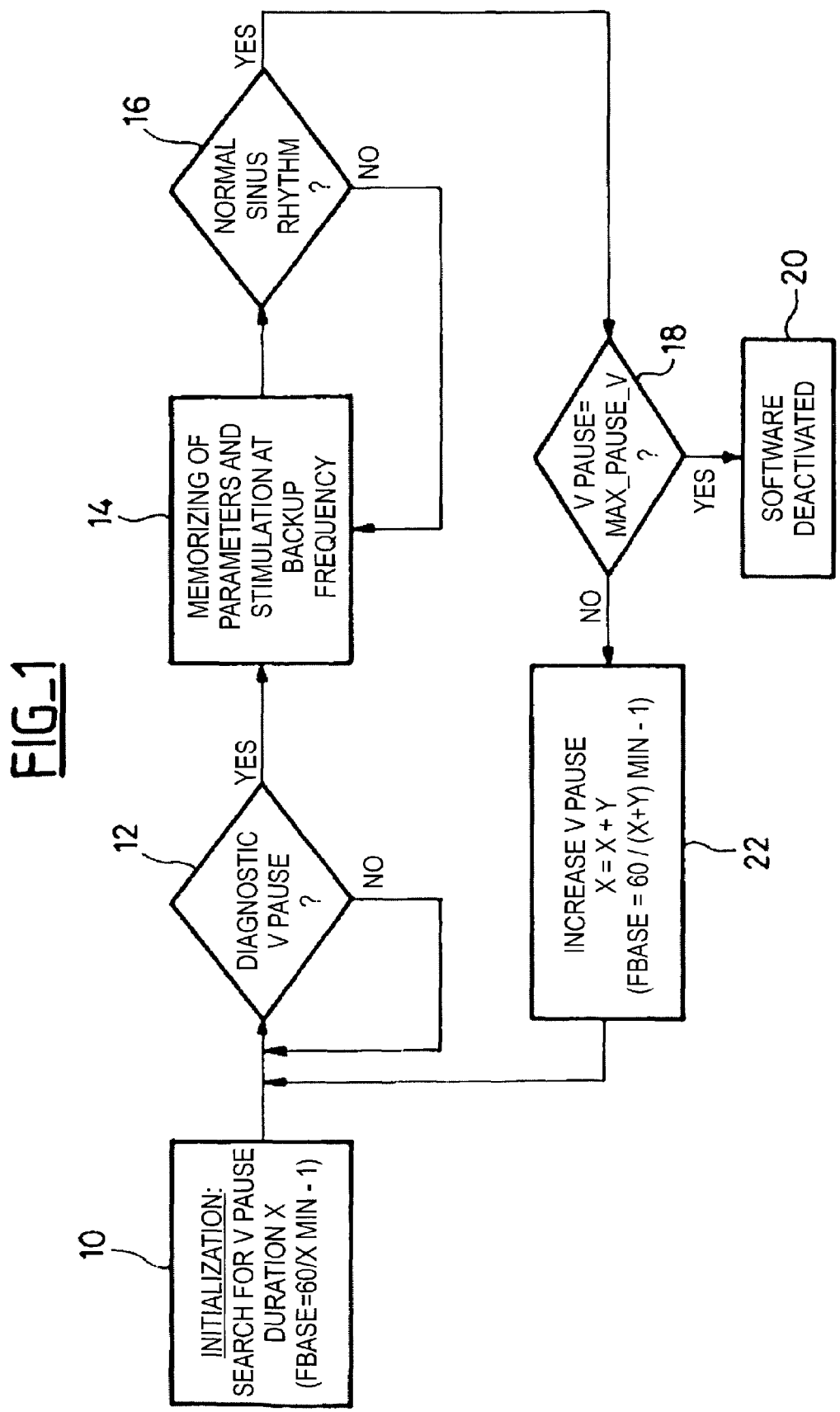
FIG. 1 illustrates a flow chart implementing an algorithm for treating heartbeat rate disorders performed by the present invention.

With reference to FIG. 1, initially (step 10), the base frequency is initialized with a value that authorizes a ventricular pause of reasonable duration, for example, a three seconds pause (i.e., a base frequency of 20 bpm). This is a very low value that is nonphysiological (i.e., located beyond the normal spontaneous rate/rhythm range), and will let possible bradycardias be expressed. The initial value of 20 bpm corresponding to a three second pause is of course given only as an example. In practice, it corresponds to a limiting value of a non-pathological ventricular pause, for example, appearing in a normal manner during a sleep phase among patients that are prone to the phenomena of apnea.

The device then measures uninterrupted the duration of the current ventricular cycle. If this duration reaches a value corresponding to the base frequency, the device then diagnoses the occurrence of a ventricular pause (step 12). This starts in turn two actions (step 14).

First is preserving the last current Holter information that was recorded before the detected ventricular pause, for example, safeguarding in memory the parameters related to the detected cardiac activity that were recorded during the three seconds preceding the beginning of the detected ventricular pause, so that subsequent recording does not overwrite or delete this preserved data. The continuously recorded Holter information typically comprises, in particular, an endocardial electrocardiogram, as well as event markers and perhaps other data relating to, for example, the minute-ventilation (a patient physiological parameter corresponding to cardiac output needs), the state of a sensor measuring effort (a patient activity parameter), etc. For convenience, the term "current cardiac information" should be understood to include one or more of such data, i.e., an electrogram, event markers, sensor or other determined parameter values, whether or not such information is normally considered to be Holter information.

Second is providing an immediate delivery of a back-up stimulation pulse at a physiological frequency, for example, 50 bpm or more (this value preferably having been programmed in advance), and continuing this activity during several cycles so as to minimize or make unperceivable the possible symptoms consequent to the ventricular pause. The back-up stimulation pulse delivered at the physiological frequency is maintained as long as a normal spontaneous rhythm is not found, such that a test for the presence of a spontaneous rhythm is conducted, for example, after a given number (e.g., ten) of stimulation cycles at the physiological frequency (step 16).

In the absence of a return to normal spontaneous rhythm, the device determines that the disorder that was suspected of being an isolated abnormality became chronic, and the patient thus needs in such an event a permanent stimulation. In the event of a re-establishment of a normal spontaneous rate/rhythm, if the last detected ventricular pause (at step 12) corresponds to the maximum value of the ventricular pause set by the practitioner (step 18), then the algorithm can be deactivated (step 20).

The device then preserves and protects the recorded current cardiac information contained in its memories, so that it will be then possible to transmit the stored data by a radio telemetry transmission of the information in the memories to an external system (i.e., a so-called programmer) for an analysis by the practicitioner. The telemetry transmission may be by any useful format, as such are known to persons of ordinary skill in the art.

In the contrary case, the device recomputes a new lower base frequency (step 22), thus authorizing a longer ventricular pause. The search for the ventricular pause (step 12) is then repeated using the new base frequency, with any stimulation at the physiological frequency having of course been stopped as of disappearance of the bradycardia (test of step 16).

The reiteration of the algorithm makes it possible to let appear, and to record, ventricular pauses of increasing severity, which will end by being perceived by the patient. This patient then will be able to consult the practitioner as of the appearance of these symptoms—the back-up stimulation remaining active in the meanwhile.

The patient thus benefits at the same time from the Holter capabilities of the implant (which will allow for a subsequent diagnosis by the practitioner) and the safety provided by the back-up stimulation, the latter being used only in those situations where it proves really necessary.

Suitable devices for which the present invention has application include, for example, the Talent™ and Symphony™ brand of pacemakers available from Ela Medical, Montrouge France. These devices are capable of receiving software instructions by telemetry, storing them in memory, and then executing those instructions to perform the functions described above in implementing the present invention. Indeed, those devices contain circuits representative of those useful for delivering stimulation pulses, monitoring cardiac activity and inhibiting the stimulation while searching for a ventricular pause. The creation of suitable software instructions for controlling an implant to perform the aforementioned functions of the present invention are believed to be within the abilities of a person of ordinary skill in the art.

One skilled in the art will appreciate that the present invention can be practiced by other than the described embodiments, which are presented for purposes of illustration and not of limitation.

I claim:

1. An active implantable double-chamber pacemaker, including:
   means for detecting spontaneous ventricular cardiac activity;
   means for detecting atrial cardiac activity;
   means for stimulating a ventricle;
   means for controlling the stimulation means to deliver a stimulation in the absence of a detected spontaneous ventricular cardiac activity;
   means for continuously recording current cardiac information representative of the detected cardiac activity;
   means for inhibiting the ventricular stimulation means for a controlled period, said controlled period being selectable;
   means for detecting a ventricular pause of duration greater than a predetermined value, said detected ventricular pause occurring during a period of controlled inhibition of the ventricular stimulation means;
   means for progressively adjusting said predetermined value;
   means for safeguarding the current cardiac information recorded during an interval preceding said detected ventricular pause;
   means for determining a bradycardia condition corresponding to said detected ventricular pause; and
   means for discriminating an origin of said bradycardia caused by a heartbeat rate disorder.

2. The device of claim 1, further comprising controlling means for controlling the ventricular stimulation means to deliver stimulation pulses at a physiological back-up frequency in response to a detected ventricular pause.

3. The device of claim 1, wherein said means for progressively adjusting said predetermined value further comprises:
   means for reducing said predetermined value by a step after each detection of a ventricular pause by the detecting means, said reduction being operated repeatedly until said predetermined value is not greater than a programmed minimum threshold.

4. The device of claim 3, wherein said reducing means is responsive to said detecting means having previously detected a normal spontaneous ventricular cardiac activity.

5. The device of claim 1, further comprising means for permanently deactivating said means for inhibiting the ventricular stimulation means, after safeguarding said last recorded current cardiac information.

6. The device of claim 5, wherein said means for progressively adjusting said predetermined value further comprises:
   means for successively reducing said predetermined value by a step after each detection of a ventricular pause by the detection means, said reduction being operated repeatedly until said predetermined value is not greater than a programmed minimum threshold;
   wherein said permanently deactivating means are used only in response to said reducing means having performed the said successive reduction until said predetermined value is not greater than the programmed threshold and after said detecting means having previously detected a normal spontaneous ventricular cardiac activity.

7. An active implantable medical device, including:
   means for detecting spontaneous ventricular cardiac activity;
   means for stimulating a ventricle;
   means for controlling the stimulation means to deliver a stimulation in the absence of a detected spontaneous ventricular cardiac activity;
   means for continuously recording current cardiac information representative of the detected cardiac activity;
   means for inhibiting the ventricular stimulation means for a controlled period, said controlled period being selectable;
   means for detecting a ventricular pause of duration greater than a predetermined value, said detected ventricular pause occurring during a period of controlled inhibition of the ventricular stimulation means;

means for progressively adjusting said predetermined value by successively reducing said predetermined value by a step after each detection of a ventricular pause by the detection means, said reduction being operated repeatedly until said predetermined value is not greater than a programmed minimum threshold;

means for safeguarding the current cardiac information recorded during an interval preceding said detected ventricular pause; and means for permanently deactivating said means for inhibiting the ventricular stimulation means after safeguarding said last recorded current cardiac information, wherein said permanently deactivating means are used only in response to said reducing means having performed the said successive reduction until said predetermined value is not greater than the programmed threshold and after said detecting means having previously detected a normal spontaneous ventricular cardiac activity.

8. The device of claim 7, wherein said active implantable medical device further comprises a double-chamber pacemaker including means for detecting an atrial cardiac activity, means for determining a bradycardia condition corresponding to said detected ventricular pause as caused by a heartbeat rate disorder; and means for discriminating an origin of said bradycardia caused by a heartbeat rate disorder.

9. The device of claim 7, further comprising controlling means for controlling the ventricular stimulation means to deliver stimulation pulses at a physiological back-up frequency in response to a detected ventricular pause.

10. The device of claim 7, wherein said means for means for progressively adjusting said predetermined value is responsive to said detecting means having previously detected a normal spontaneous ventricular cardiac activity.

* * * * *